US012693282B2

(12) United States Patent
Trehan et al.

(10) Patent No.: US 12,693,282 B2
(45) Date of Patent: Jul. 28, 2026

(54) DETERMINING PROTEIN CONTENT OF PROTEIN SUPPLEMENTS AND DETERMINING GENUINE OR COUNTERFEIT PROTEIN SUPPLEMENTS WITH A NOVEL CONSUMER FRIENDLY KIT

(71) Applicant: Bright Lifecare Pvt. Ltd., Haryana (IN)

(72) Inventors: Anupam Trehan, Haryana (IN); Manoj Kumar Verma, Haryana (IN); Raman Kumar Matta, Haryana (IN); Harinder Singh, Haryana (IN); Shubham Pachauri, Haryana (IN); Akash Jangra, Haryana (IN); Sameer Maheshwari, Haryana (IN)

(73) Assignee: Bright Lifecare Pvt. Ltd., Haryana (IN)

( * ) Notice: Subject to any disclaimer, the term of this patent is extended or adjusted under 35 U.S.C. 154(b) by 654 days.

(21) Appl. No.: 17/871,160

(22) Filed: Jul. 22, 2022

(65) Prior Publication Data

US 2023/0040075 A1     Feb. 9, 2023

(30) Foreign Application Priority Data

Aug. 4, 2021    (IN) ............................... 20211035201

(51) Int. Cl.
*G01N 33/02*     (2006.01)
*G01N 33/68*     (2006.01)
*G01N 1/40*     (2006.01)

(52) U.S. Cl.
CPC ............. *G01N 33/02* (2013.01); *G01N 33/68* (2013.01); *G01N 33/6827* (2013.01); *G01N 1/4055* (2013.01)

(58) Field of Classification Search
CPC .... G01N 33/02; G01N 33/68; G01N 33/6827; G01N 1/4055; G01N 2001/027; Y10T 436/25; Y10T 436/25375
USPC ............. 436/20, 86, 174, 177; 422/430, 527
See application file for complete search history.

(56) References Cited

U.S. PATENT DOCUMENTS 3,970,746 A * 7/1976 Premachandra ....... G01N 33/78
424/1.49
5,571,334 A * 11/1996 Dunn .................... A23L 29/212
127/29

FOREIGN PATENT DOCUMENTS

| CN | 201382930 Y | * | 1/2010 |
| CN | 104406960 A | * | 3/2015 |
| CN | 106872455 A | * | 6/2017 |
| WO | 91/19193 | * | 12/1991 |

* cited by examiner

*Primary Examiner* — Maureen Wallenhorst
(74) *Attorney, Agent, or Firm* — Liang & Hennessey LLP; Stanley D. Liang

(57) ABSTRACT

The present invention relates to a user friendly and cost effective kit for determining the protein content in protein supplements and determining if the protein supplement is a genuine or a counterfeit protein supplement in a home setting. Furthermore, the present invention also details the method of using the kit.

1 Claim, No Drawings

DETERMINING PROTEIN CONTENT OF PROTEIN SUPPLEMENTS AND DETERMINING GENUINE OR COUNTERFEIT PROTEIN SUPPLEMENTS WITH A NOVEL CONSUMER FRIENDLY KIT

FIELD OF THE INVENTION

The present invention relates to a user friendly and cost effective kit for determining the protein content in protein supplements and determining if the protein supplement is a genuine or a counterfeit protein supplement in a home setting. Furthermore, the present invention also details the method of using the kit.

BACKGROUND OF THE INVENTION

Protein supplements are one of the most widely consumed supplements by athletes and physically active individuals. There is a global consensus that around 0.8-0.9 g protein/kg of body weight could satisfy adult protein needs. Recent reviews focus on the use of dietary recommendations for protein among active individuals such as athletes. There is a general consensus that protein needs for active individuals are higher than the sedentary one. Intakes of 1.2-1.4 g protein/kg of body weight for endurance athletes and 1.2-1.7 g protein/kg of body weight for power athletes have been suggested as appropriate requirements. Amongst the ingredients used to manufacture this type of product (i.e. casein- ates, whey, egg, soy, and wheat proteins), whey protein is the most commercialized in the sports nutrition market due to its high nutritional value when compared to other proteins sources. Whey protein represents 20-30% of the proteins present in bovine milk; it is a complex mixture of globular protein molecules consisting mostly of α-lactalbumin (α-La), β-lactoglobulin (β-Lg). The protein fractions α-La and β-Lg (variants A and B) represent almost 70% of the proteins present in whey. Differences in the physical-chemical composition of whey protein supplements potentially influence its nutritional effect on the human body. The nutritional quality of whey protein supplement depends on amino acid composition, bioavailability of essential amino acids, protein digestibility, and physiological utilization of specific amino acids after digestion and absorption. Whey protein is considered an important source of essential amino acids, of which the branched-chain amino acids leucine, isoleucine and valine have been associated with increased stimulus of skeletal muscle protein synthesis.

The consumption of supplements by athletes and fitness enthusiasts to improve exercise performance has been increasing over the last few years. In some cases, users expect the supplements to fulfil nutritional needs created by an incomplete diet, while in other cases they expect the supplements to enhance their sports performance. However, there is not a consensus among physicians and trainers regarding the benefits of nutritional supplements, because of an enormous quantity of contaminated, fake, counterfeit or ineffective supplements that might pose serious risks to an athlete's health or lead to evidence of doping in adverse analytical findings. Whey protein is a soluble protein fraction in milk serum that is obtained during cheese and casein production, has been studied since the 1970s as a source of high biological-value proteins, as well as bioactive peptides, which might act as antimicrobial, antihypertensive, and immune response modulator agents. A controlled study of 874 athletes in the UK showed that approximately 60%

(520) of the athletes use some type of nutritional supplement. The most popular performance-related supplements were creatine, which was used by 36.1% of the supplement-using athletes, followed by whey protein-based supplements, which were adopted by 30.6% of the users. However, this study has shown that many athletes do not know the reasons why they use a given supplement or, worse, they might use a supplement for a reason that is not compatible with the proven effects of that substance. Unfortunately, the adulteration is extremely common in products derived from powdered milk, the most common cases being the addition of compounds.

Often the athletes or bodybuilders consult their gym instructors for guidance on bodybuilding supplements who themselves have limited knowledge. They suggest supplements which are available at cheaper rates. These are usually spurious products from the grey market. Usually the people from the bodybuilding fraternity buy supplements from local pharmacy, local supplement stores or through online channels.

The consumer can check the authenticity of the products via unique authentication code inside or above the pack which they can use to verify their purchase, but still the quality of the product is a big question for them.

It is not possible to check their products as many of them are not aware about the laboratories that can do the test on protein content. Moreover it is not economically feasible to check the protein content every time the consumer buys the supplement as it would be a costly activity.

There are different methods used in laboratories for the estimation of protein such as Kjeldahl method, UV-visible spectroscopy method, Biuret Method, Lowry Method, Dye Binding methods and Turbimetric method.

These methods are complex and can be performed in a laboratory set-up only by a skilled analyst. There are no readily available and consumer friendly methods for the consumers to check the protein content at their home.

The inventors of the present invention have developed a user friendly and cost effective kit for determining the protein content in protein supplements in a home setting to make consumers more aware and confident of the products they are using on routine basis for the intended benefit. Furthermore, the present invention also details the method of using the kit.

SUMMARY OF THE INVENTION

It is an object of the present invention to provide a kit for the determination of protein content in a protein supplement by the consumer in a home setting.

It is another object of the invention to provide a method for determination of the protein content in a protein supplement using the kit wherein the method is carried out by the consumers themselves.

It is another object of the invention to provide a method for determination of protein content in a protein supplement wherein the method reduces requirement of complex laboratory apparatus and chemical reagents and the consumer can carry out the method in a simple setup such as a home.

It is another object of the invention to provide a kit and a method for determining if the protein supplement is a genuine protein supplement or a counterfeit protein supplement. The method can be carried out by the consumer in a home setting.

In one general aspect, the present invention provides a kit for quantitative measurement of for determination of protein content in a protein supplement wherein the kit comprises:

a graduated tube with markings to measure the amount of precipitate;

a non-graduated tube or a vial containing the protein precipitation solution; and a protein measurement chart with precipitate volume in millilitres indicating corresponding amount of protein as percentage.

In one embodiment of the above aspect, the protein precipitation solution contains trichloroacetic acid (TCA) in an amount of about 30% w/v solution.

In another embodiment of the above aspect, the protein precipitation solution is packed in a container for storage and use.

In another embodiment of the above aspect, the method is performed by the consumer in a home setting.

In another embodiment of the above aspect, the protein supplement is a whey protein supplement.

In another general aspect, the method of using the kit comprises:

dissolving/suspending the measured quantity of the protein supplement in a fixed quantity of water in a container, taking a fixed portion of the above solution/suspension in a graduated tube and adding the protein precipitation solution and shaking the contents for a fixed amount of time, leaving the graduated tube on standby overnight, measuring the level of precipitate in the graduated tube based on the markings; and tallying the corresponding precipitate volume from the protein measurement chart and calculate the percentage of protein.

In an embodiment of the above aspect, the measured quantity of protein supplement is up to 30 grams.

In another embodiment of the above aspect, the quantity of water is about 200 mL.

In another embodiment, the protein precipitation solution contains trichloroacetic acid (TCA) in an amount of about 30% w/v of the solution.

In another embodiment of the above aspect, the final volume of the protein precipitation solution is made up to 100% with water.

In yet another aspect, the invention relates to the method of using the kit to differentiate between a genuine protein supplement and a counterfeit supplement wherein the method comprises:

dissolving/suspending the measured quantity of the protein supplement in a fixed quantity of water in a container, taking a fixed portion of the above solution/suspension in a graduated tube and adding the protein precipitation solution and shaking the contents for a fixed amount of time, leaving the graduated tube on standby overnight (18-24 hours);

inverting the above graduated tube with the precipitate;

observing if the precipitate remains intact and does not fall down within a few seconds or the whole precipitate does not mix with the solution and concluding that the protein supplement is a genuine protein supplement; or observing if the precipitate re-disperses and mixes with the contents of the graduated tube and concluding that protein supplement is a counterfeit protein supplement.

In an embodiment of the above aspect, the measured quantity of protein supplement is up to 30 grams.

In another embodiment of the above aspect, the quantity of water is about 200 mL.

In another embodiment, the protein precipitation solution contains trichloroacetic acid (TCA) in an amount of about 30% w/v of the solution.

In another embodiment of the above aspect, the final volume of the protein precipitation solution is made up to 100% with water.

In yet another aspect, the invention relates to the method of using the kit to differentiate between a genuine protein supplement and a counterfeit protein supplement wherein the method comprises:

dissolving/suspending the measured quantity of the protein supplement in a fixed quantity of water in a container, taking a fixed portion of the above solution/suspension in a graduated tube and adding the protein precipitation solution and shaking the contents for a fixed amount of time, leaving the graduated tube on standby overnight (18-24 hours);

precipitate is scooped out of the graduated tube by a spatula or a spoon like device and observing if a thick and uniform precipitate comes out, concluding that the protein supplement is a genuine protein supplement; or precipitate is scooped out of the graduated tube by a spatula or a spoon like device and observing if precipitate comes out as a watery precipitate rather than a thick uniform paste, concluding that the protein supplement sample is a counterfeit protein supplement.

In an embodiment of the above aspect, the measured quantity of protein supplement is up to 30 grams.

In another embodiment of the above aspect, the quantity of water is about 200 mL.

In another embodiment, the protein precipitation solution contains trichloroacetic acid (TCA) in an amount of about 30% w/v of the solution.

In another embodiment of the above aspect, the final volume of the protein precipitation solution is made up to 100% with water.

DETAILED DESCRIPTION OF THE INVENTION

The present invention provides a method and a kit for quantitative determination of protein content in a protein supplement such a whey protein supplement. The method works on the principle of hydrophobic aggregation in which the protein precipitation solution precipitate outs the protein present in the protein supplement such as whey protein. The protein precipitation solution is a ready to use solution packed in a suitable container for use by the consumer to test the protein supplements in an environment that does not require sophisticated instruments and costly reagents of an analytical laboratory. The protein precipitation solution is prepared by dissolving a weighed quantity of trichloroacetic acid in an amount of water and making up the desired volume with water. For example, to make 100 mL of the protein precipitation solution, about 30 grams of trichloroacetic acid is dissolved in 50 mL of water. Optionally, to this solution 10 mL of ethanol is added and the final volume of 100 mL is made with water. Ethanol if used can be present in an amount of about 5% to 20%, preferably about 10%. The solution can then be packed in the form of kit. The kit may comprise of a container containing the protein precipitation solution and a graduated container such as a centrifuge tube or a graduated tube. The kit can optionally also contain a shaker for preparing the solution/suspension of the protein supplement in water. Alternatively, the consumer can use any suitable container readily available to prepare the solution/suspension of the protein supplement.

The protein precipitation solution is effective at lower amounts than the other precipitation reagents ~30% for TCA helps to denature the protein. Further, it does not affect total protein content in the sample and the precipitate can be further analyzed by standard methods. The method precipitates the proteins independently of their physicochemical properties.

The method is further made easy to perform with the help of the kit. The kit comprises a graduated tube with markings to measure the volume of precipitate; a non-graduated tube or a vial containing the protein precipitation solution; and a protein measurement chart indicating precipitate volume in millilitres and its corresponding amount of protein as percentage. The graduated tube may have a length of about 120 mm and a diameter of about 25 mm with 1 mL least count. The non-graduated glass tube or vial may contain about 30 mL to 40 mL of protein precipitation solution, preferably 35 mL.

Further, the method can also be used to test whether the protein supplement is a genuine protein supplement or a counterfeit supplement. For example, after measuring the precipitate volume, the graduated tube can be inverted to observe if the precipitate remains intact and does not fall down or the whole precipitate does not mix with the solution. If so observed then it can be concluded that the protein supplement sample is a genuine protein supplement. If it is observed that the precipitate mixes in a few seconds or the whole precipitate mixes with the contents of the tube then it can be concluded that the protein supplement sample is a counterfeit protein supplement. Alternatively, the same method can be followed by using a spatula or a spoon like device. The precipitate is scooped out of the graduated tube by a spatula and if a thick and uniform precipitate comes out, then it can be concluded that the protein supplement sample contains genuine protein supplement. If the precipitate comes out as a watery precipitate rather than a thick uniform paste, then it can be concluded that the protein supplement sample is a counterfeit protein supplement.

TABLE 1

| | Protein Measurement Chart | |
| S. No. | Precipitation (in mL) | Corresponding Protein Content (%) |
| --- | --- | --- |
| 1 | 6 mL-7 mL | 35-45% |
| 2 | 7 mL-8 mL | 45-55% |
| 3 | 8 mL-9 mL | 55-65% |
| 4 | 9 mL-10 mL | 65-75% |
| 5 | 10 mL-11 mL | 75-85% |
| 6 | >11 ml | More than 85 % |

The method can be performed by steps as follows:
1. Take 30 g of protein supplement powder in 200 ml of drinking water (8-15° C.) in a Shaker bottle and mix the protein supplement powder with manual shaking for 15 to 30 seconds;
2. In a graduated tube add 35 mL of protein precipitation solution.
3. To the above graduated tube add 10 mL of the protein powder solution/suspension of step 1.
4. Shake the graduated tube for 60 seconds and keep it in vertical position overnight at room temperature.

5. Measuring the precipitate volume in the graduated tube and tallying the corresponding volume from the protein measurement chart indicating corresponding amount of protein as percentage.

The same test kit can also be used to determine if the protein supplement sample is genuine or a counterfeit supplement. The method can be performed after the protein precipitation solution and the protein powder solution/suspension have been mixed in the graduated tube as that in Step 4 above. If about one minute of mixing, some precipitate will float at the top of the solution, while some precipitate will start settling at the bottom of the tube as a coagulate i.e. the supplement tested contains protein such as a whey protein. If mixture is uniformly spread out in the same colour as of the initial dispersion that was poured, without any separation or precipitation at all, it is the first indicator that the tested protein supplement could actually be a counterfeit. It could be a flour with maltodextrin-some kind of carbohydrate or even a non-food item. After five minutes, if there is even more separation of the precipitate settling at the base of the tube as a coagulate and the precipitate floating at the top of the tube becomes thinner and the solution in the middle starts to become clearer it can be concluded that supplement tested does contain protein and is a genuine protein supplement. In another scenario, after five minutes, the mixture is still uniformly spread out in the same color with not much difference from the first observation five minutes earlier and is still without any separation or precipitation, it can be concluded that the supplement tested is counterfeit protein supplement.

The test method of the invention can check the amount of protein in any protein sample and several marketed whey protein supplement products were tested by this novel method. Table 2 provides the results of testing the protein content of some commercially available protein supplements.

All the results were confirmed in the Laboratory through quantitative analysis of the same samples using standard Kjeldahl method for protein content. The recovery for the entire sample was found to be approximately 95% as per the label claim.

This method is fast, reliable and consumer friendly which can be done at home using the kit. The purpose of this study was to transfer the complex laboratory method to the consumer's home where anyone can test the quality and genuineness of the protein supplements. This way consumer can become more aware and confident of the quality of the protein supplement such as whey protein they have purchased from the source.

TABLE 2

| | Protein Content of Some Commercial Protein Supplements Determined by the Protein Precipitation Method Using the Kit of the Invention. | | | | |
| Products | (80%) MB Raw Whey ® | MB Beginner's Protein ® | Pro Burst ® | MB Biozyme Whey ® | MB Whey Gold ® |
| --- | --- | --- | --- | --- | --- |
| Approximate Protein Content by standard method | 80% | 40% | 73% | 76% | 83% |
| Over night results | >11 mL | 6-7 mL | 9-10 mL | 10-11 mL | 10-11 mL |
| Determined Content | 80%+ | 40% | 73% | 75+% | 80+% |

TABLE 2-continued

| | (80%) MB Raw Whey ® | MB Beginner's Protein ® | Pro Burst ® | MB Biozyme Whey ® | MB Whey Gold ® |
|---|---|---|---|---|---|
| Products | | | | | |

Protein Content of Some Commercial Protein Supplements Determined by the Protein Precipitation Method Using the Kit of the Invention.

(Kjeldahl method)

We claim:

1. A kit for quantitative determination of protein content in a whey protein supplement, the kit consisting of:

(1) a shaker bottle for mixing a protein supplement powder by manual shaking;

(2) a graduated tube with markings to measure amount of protein precipitate in said whey protein supplement;

(3) a non-graduated tube containing a protein precipitation solution wherein the protein precipitation solution contains trichloroacetic acid (TCA) in an amount of 30% w/v and ethanol in an amount of 5% to 20%; and (4) a protein measurement chart specifically calibrated for whey protein with precipitate volume in milliliters indicating corresponding amount of protein as percentage;

wherein said kit is for quantitative determination of protein content in a whey protein supplement by a consumer in a home setting, in an environment that does not require sophisticated instruments of a laboratory, and not in a laboratory setting.

* * * * *